US012559744B2

(12) United States Patent
Opijnen et al.

(10) Patent No.: US 12,559,744 B2
(45) Date of Patent: Feb. 24, 2026

(54) METHOD FOR APTAMER SELECTION AND IDENTIFICATION

(71) Applicant: The Trustees of Boston College, Chestnut Hill, MA (US)

(72) Inventors: Tim van Opijnen, Somerville, MA (US); Juan C. Ortiz-Marquez, Brighton, MA (US); Stephen Hummel, Ft. Myers, FL (US); José Bento, Medfield, MA (US)

(73) Assignee: The Trustees of Boston College, Chestnut Hill (MA)

( * ) Notice: Subject to any disclaimer, the term of this patent is extended or adjusted under 35 U.S.C. 154(b) by 944 days.

(21) Appl. No.: 17/827,240

(22) Filed: May 27, 2022

(65) Prior Publication Data

US 2022/0389407 A1 Dec. 8, 2022

Related U.S. Application Data

(60) Provisional application No. 63/195,864, filed on Jun. 2, 2021.

(51) Int. Cl.
*C12N 15/10* (2006.01)
*C12Q 1/6811* (2018.01)

(52) U.S. Cl.
CPC ........ *C12N 15/1048* (2013.01); *C12Q 1/6811* (2013.01)

(58) Field of Classification Search
CPC .......... C12N 15/1048; C12N 2525/205; C12Q 1/6811; C12Q 2525/205; C12Q 2541/101
See application file for complete search history.

(56) References Cited

U.S. PATENT DOCUMENTS 9,315,804 B2 * 4/2016 Brown ............... C12N 15/1048
2019/0024087 A1 * 1/2019 Ochsner ............... C12N 15/115

OTHER PUBLICATIONS

Mousivand et al. (Analytica Chimica Acta, 2020, 1105:178e186) (Year: 2020).*
Ellington, AD and Szostak, JW (1990). In vitro selection of RNA molecules that bind specific ligands. Nature 346: 818-822.
Tuerk, C and Gold, L (1990). Systematic evolution of ligands by exponential enrichment: RNA ligands to bacteriophage T4 DNA polymerase. Science 249: 505-510.
Cho, E. J., Lee, J. W. & Ellington, A. D. Applications of aptamers as sensors. Annu. Rev. Anal. Chem. 2, 241-264 (2009).
Slaats, Jeroen, et al. "IL-1β/IL-6/CRP and IL-18/ferritin: distinct inflammatory programs in infections." PLoS pathogens 12.12 (2016).

Irvine, D., Tuerk, C., & Gold, L., 1991. Selexion: Systematic evolution of ligands by exponential enrichment with integrated optimization by non-linear analysis. Journal of molecular biology, 222(3), 739-761.
Liu, D., Hu, B., Peng, D., Lu, S., Gao, S., Li, Z., . . . & Jiao, B., 2020. Isolation ssDNA aptamers specific for both live and viable but nonculturable state Vibrio vulnificus using whole bacteria—SEILEX technology. RSC Advances, 10(27), 15997-16008.
Wang, J., Gong, Q., Maheshwari, N., Eisenstein, M., Arcila, M. L., Kosik, K. S., & Soh, H. T., 2014. Particle Display: A Quantitative Screening Method for Generating High-Affinity Aptamers. Angewandte Chemie International Edition, 53 (19), 4796-4801.
Mirzakhani, K., Gargari, S. L. M., Rasooli, I., & Rasoulinejad, S., 2018. Development of a DNA aptamer for screening Neisseria meningitidis Serogroup B by cell SELEX. Iranian biomedical journal, 22(3), 193.
Song, Y., Song, J., Wei, X., Huang, M., Sun, M., Zhu, L., . . . & Yang, C., 2020. Discovery of Aptamers Targeting Receptor-Binding Domain of the SARS-CoV-2 Spike Glycoprotein.
H.M. Berman, J. Westbrook, Z. Feng, G. Gilliland, T.N. Bhat, H. Weissig, I.N. Shindyalov, P.E. Bourne (2000) The Protein Data Bank Nucleic Acids Research, 28: 235-242.
Luscombe NM, Laskowski RA, Thornton JM. Amino acid-base interactions: a three-dimensional analysis of protein-DNA interactions at an atomic level. Nucleic Acids Res. 2001;29(13):2860-2874. doi:10.1093/nar/29.13.2860.
Hoffman MM, Khrapov MA, Cox JC, Yao J, Tong L, Ellington AD. AANT: the Amino Acid-Nucleotide Interaction Database. Nucleic Acids Res. 2004;32 (Database issue): D174-D181. doi:10.1093/nar/gkh128.
Park, B., Kim, H. & Han, K. DBBP: database of binding pairs in protein-nucleic acid interactions. BMC Bioinformatics 15, S5 (2014).
Antczak, M., Popenda, M., Zok, T., Sarzynska, J., Ratajczak, T., Tomczyk, K., Adamiak, R.W., Szachniuk, M. New functionality of RNAComposer: an application to shape the axis of miR160 precursor structure, Acta Biochimica Polonica, 2016, 63(4):737-744 (doi:10.18388/abp.2016_1329).

(Continued)

*Primary Examiner* — Jeremy C Flinders
(74) *Attorney, Agent, or Firm* — Lei Fang, Esq.; Smith Tempel Blaha LLC

(57) ABSTRACT

The present disclosure provides a novel approach, recomSELEX, that highly integrate mutually supportive recombination and computational methods for aptamer selection and identification. The recomSELEX approach comprises a recombinatorial SELEX platform for aptamer screening that exponentially increases the sequence space that is explored by incorporation of a DNA shuffling step that allows recombination between aptamers. Subsequently, the recombinatorial SELEX platform can also be employed to develop new and optimize already existing aptamers. The recomSELEX further comprises a computational SELEX platform with a constrained genetic algorithm (GA) to identify potential aptamers that are stable and have the desired specificity and affinity of a target.

18 Claims, 5 Drawing Sheets

Specification includes a Sequence Listing.

(56)            References Cited

OTHER PUBLICATIONS

Popenda, M., Szachniuk, M., Antczak, M., Purzycka, K.J., Lukasiak, P., Bartol, N., Blazewicz, J., Adamiak, R.W. Automated 3D structure composition for large RNAs, Nucleic Acids Research, 2012, 40(14):e112 (doi:10.1093/nar/gks339).

* cited by examiner

Figure 2:
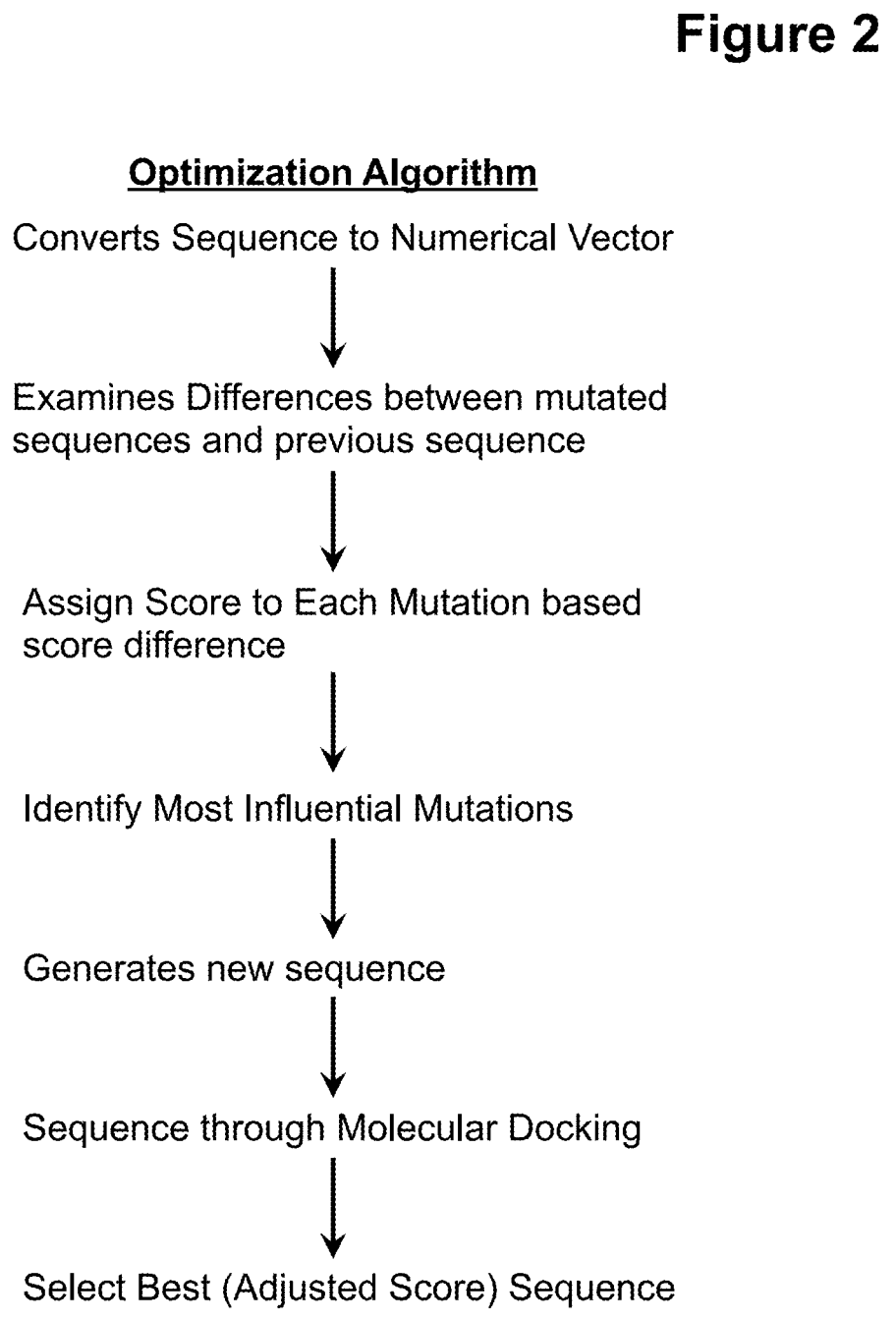

Optimization Algorithm

Converts Sequence to Numerical Vector

↓

Examines Differences between mutated sequences and previous sequence

↓

Assign Score to Each Mutation based score difference

↓

Identify Most Influential Mutations

↓

Generates new sequence

↓

Sequence through Molecular Docking

↓

Select Best (Adjusted Score) Sequence

CAGCACCGACCTTGTGCTTTGGGAGTGCTGGTCCAAGGGCGTTAATGGACA

1C ~ Genetic Algorithm (GA)

*TTTTG*CAGCACCGACCTTGTGCTTTGGGAGTGCTGGTCCAAGGGCGTTAATGGACA

1C- AntiSense

*GGGGT*CAGCACCGACCTTGTGCTTTGGGAGTGCTGGTCCAAGGGCGTTAATGGACA

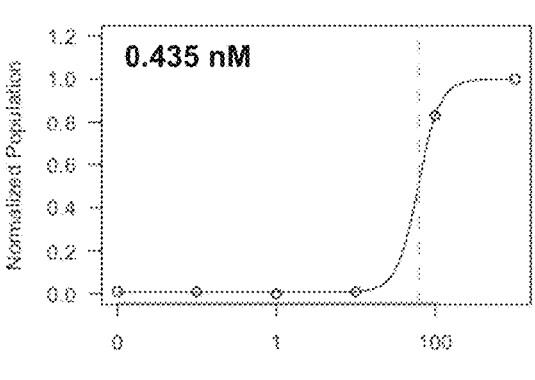

4C

TCCAGAGTGACGCAGCATTTCATCGGGTCCAAAAGGGGCTGCTCGGGATTGCGGATATGGACACGT

4C ~ Genetic Algorithm (GA)

*CTAAGGCA*TCCAGAGTGACGCAGCATTTCATCGGGTCCAAAAGGGGCTGCTCGGGATTGCGGATATGGACACGT

4C- AntiSense

*ACGGTTAGT*CCAGAGTGACGCAGCATTTCATCGGGTCCAAAAGGGGCTGCTCGGGATTGCGGATATGGACACGT

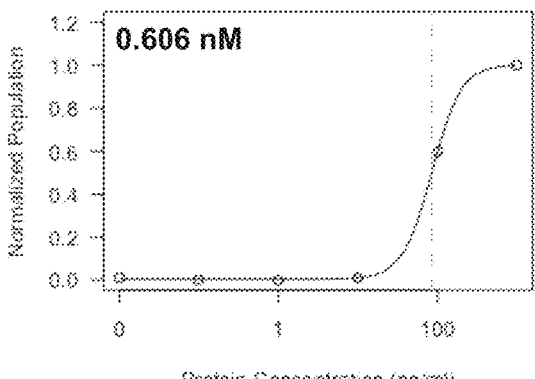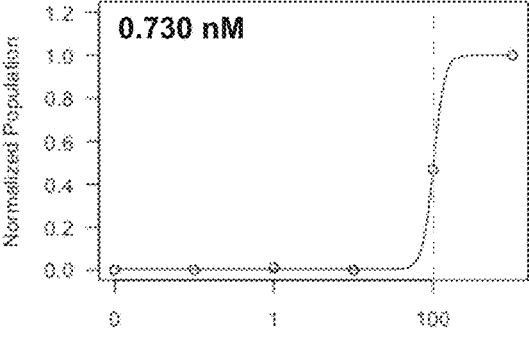

SEQUENCE LISTING

<160> NUMBER OF SEQ ID NOS: 14

<210> SEQ ID NO 1
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaacccgtag tggcctcata agtgctcaga cgaggactag agcaccgaaa aggcagggag      60
gctagtctcc cgaatgcggg ccg                                            83

<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agttggttat tttgtggtgg tagacgagga ctagagcacc gaaaaattta tggaataggt      60
agagaatt                                                             68

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acaacgttta ctaacctatt cgctacgagg actagagcac cgaaaagtac ttctttggct      60
acatacgacg gtgta                                                     75

<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagcccgttg ttgcttgtct ttttctacga ggactagagc accgaaaact ttatatggtt      60
tcgtggcaat agtatt                                                    76

<210> SEQ ID NO 5
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 caggggtaa cgaggggttc aacgaggact agagcaccga aaacctactt aggattgtgt        60
ctcctgcctc tgg                                                       73

<210> SEQ ID NO 6

```
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
accaccggtg ccggcatgtt gagacgagga ctagagcacc gaaaagttct ttggagcata      60
ggtaagacga cttaacg                                                     77

<210> SEQ ID NO 7
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cccctatcgt tcgcttmcgc tggatacgag gactagagca ccgaaaatgt ttaggtagac      60
cgttatcggc cgag                                                        74

<210> SEQ ID NO 8
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
taccgcgagt taggccaggg cagaaacgag gactagagca ccgaaaacgg ggcgttgatc      60
aagtgttcct tccggataca cg                                               82

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cagcaccgac cttgtgcttt gggagtgctg gtccaagggc gttaatggac a               51

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ttttgcagca ccgaccttgt gctttgggag tgctggtcca agggcgttaa tggaca          56

<210> SEQ ID NO 11
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
```

-continued

```
ggggtcagca ccgaccttgt gctttgggag tgctggtcca agggcgttaa tggaca          56

<210> SEQ ID NO 12
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tccagagtga cgcagcattt catcgggtcc aaaaggggct gctcgggatt gcggatatgg          60
acacgt                                                                    66

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctaaggcatc cagagtgacg cagcatttca tcgggtccaa aaggggctgc tcgggattgc          60
ggatatggac acgt                                                           74

<210> SEQ ID NO 14
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
acggttagtc cagagtgacg cagcatttca tcgggtccaa aaggggctgc tcgggattgc          60
ggatatggac acgt                                                           74
```

METHOD FOR APTAMER SELECTION AND IDENTIFICATION

CROSS-REFERENCE TO RELATED APPLICATIONS

This application claims the benefit of U.S. Provisional Application No. 63/195,864, filed on Jun. 2, 2021, which is incorporated herein by reference in its entirety.

STATEMENT REGARDING FEDERALLY SPONSORED RESEARCH OR DEVELOPMENT

This invention was made with government support under grant number U01 A1124302, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 21, 2022, is named 940203-1110_SL.txt and is 4,422 bytes in size.

BACKGROUND

Aptamers are short (~20-100 nucleotides), single-stranded oligonucleotides, made of DNA or RNA. They have been found to possess specificity and affinity values (dissociation constants ($K_d$)) to specific targets in the pico- to nanomolar range and have been used in a variety of fields.[1],[2] Akin to proteins, the nucleotide sequence of an aptamer gives rise to a secondary and tertiary structure, which provides it its function. The stability, ease of chemical modification (e.g., fluorophores, biotinylating and more)[3], and high specificity and affinity has enabled aptamers to be used in a variety of applications to include therapeutics, diagnostics, and as biorecognition elements on biosensors for detection of pathogens or molecules in food, the environment, and patient samples.

Systematic Evolution of Ligands by EXponential enrichment (SELEX) is the current method of aptamer development and identification. This technique has been used to select aptamers against various targets to include ions, small molecules, membrane receptors, and whole cells. The SELEX concept is essentially an in vitro optimization process for identifying aptamers with high specificity and affinity, yet it is still a lengthy and expensive process. The high costs are associated with the production of the initial random library (~$10^{15}$ molecules), sequencing, primers, target molecules (e.g., biotinylated proteins), fluorophores, and so forth. Additionally, the time required for cell culture, sequencing, and characterization of numerous potential aptamers makes the standard SELEX methods a lengthy process.

SUMMARY

In accordance with the purpose(s) of the present disclosure, as embodied and broadly described herein, the disclosure, in one aspect, provides a novel approach, referred hereinafter as recomSELEX, a platform of mutually supportive recombination and computational methods which reduce the time required for aptamer identification, cost, and is capable of exploring oligonucleotide sequences beyond the initial random library. The recomSELEX approach has an experimental and computational part that are tightly integrated; the combination of which is novel on itself. Several aspects of this platform are innovative. Conceptually innovative is accelerating the screening process for selecting highly specific aptamers with high affinity via a platform that incorporates both aptamer design and aptamer recombination through a DNA shuffling step during each round of selection. Moreover, a critical technical advance is the ability to design aptamers against a pathogen or molecule through the novel incorporation of a genetic optimization algorithm. This algorithm generates aptamers around a designated core sequence which can be against a specific amino acid sequence or a conserved sequence in aptamer series (e.g., P12-series aptamers). The algorithm uses the free energy of the sequence folding and any user defined penalties to optimize towards a novel sequence through successive generations.

In certain embodiments, the present disclosure provides a method, namely, recomSELEX, for selecting and identifying aptamers with high specificity and affinity against a target of interest. The recomSELEX method comprises the following:
   a) Performing recombinatorial SELEX (Systematic Evolution of Ligands by EXponential enrichment) for screening, selecting, identifying, and characterizing aptamers against the target of interest, and
   b) Integrating Computational SELEX with a constrained genetic algorithm (GA) to further identify and characterize the aptamers that are stable and have the desired specificity and affinity against the target of interest.

In certain embodiments, the recombinatorial SELEX comprises two-counter-selection steps which remove aptamers with no or low target-specificity, a positive selection step which selects aptamers with high affinity, and a DNA shuffling step which is added to a counter-, positive-, and counterselection steps that allows recombination between aptamers. The recombination between aptamers exponentially increases explorable sequence spaces. The counter-selection steps, the positive selection steps and the DNA shuffling step are combined with sequencing for fast and efficient aptamer identification and bioinformatic analysis for aptamer specificity and affinity. The present disclosure provides that the recombinatorial SELEX can be performed in several rounds, preferably, 1 round, 2 rounds, 3 rounds, 4 rounds, 5 rounds, 6 rounds, 7 rounds, 8 rounds, 9 rounds, and 10 rounds, in which recombination steps can be performed repeatedly to enrich for aptamers with high affinity. In certain embodiments, the recombinatorial SELEX was performed for four (4) to six (6) rounds to enrich aptamers with high affinity.

In certain embodiments, the recomSELEX method comprises an integrated Computational SELEX with a constrained genetic algorithm (GA) which is integrated with rnafold function and/or recombines oligonucleotide sequences around a target specific core sequence. In certain embodiments, the core sequence is designed and conducted in a de novo design module ("ColdStart") that selects an accessible amino acid sequence on target protein as visualized using a protein data bank file. In other embodiments, the core sequence can be designed with a method that identifies a conserved core sequence in a series of aptamers previously identified through another SELEX method.

After a list of sequences, structural information and free energy of folding is generated through recombination generations. The sequences are converted into their two- and three-dimensional structures, which then imported into an in silico counter-selection module using, for instance, a molecular docking approach, in which the designed sequence undergoes several rounds of mutations and molecular docking and the sequence with a highest affinity for the target is identified and in interaction with a non-target is minimized.

In certain embodiments, the Computational SELEX further comprises an optimization module that applies a genetic algorithm and constraints to the sequence to ensure the structure of the sequence aligns with a desired application. The optimization process moves through sequential generations identifying elite sequences and cross-over to identify a best sequence.

The present disclosure further provides that the target of interest can be ions, small molecules, membrane receptors, peptides, proteins, microorganisms, pathogens, cells, oligonucleotides, drugs, and environmental contaminants Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

FIG. 1. digitalSELEX process schematic. FIG. 1 discloses SEQ ID NOS 1-8, respectively, in order of appearance.

FIG. 2. Flow Chart of ColdStart—de novo Design.

FIG. 3. The genetic algorithm modified sequences for 1C and 4C aptamers as well as anti-sense additions. The dissociation constant (Kd) value was measured using flow cytometry. The Kd values for the 1C-GA and 4C-GA are lower than their corresponding anti-sense oligonucleotides illustrating the algorithm generated sequences and in turn structures that maintain the high affinity of the original 1C and 4C aptamers which structure precluded from measurement in the same manner. FIG. 3 discloses SEQ ID NOS 9-14, respectively, in order of appearance.

DETAILED DESCRIPTION

Figure 4:
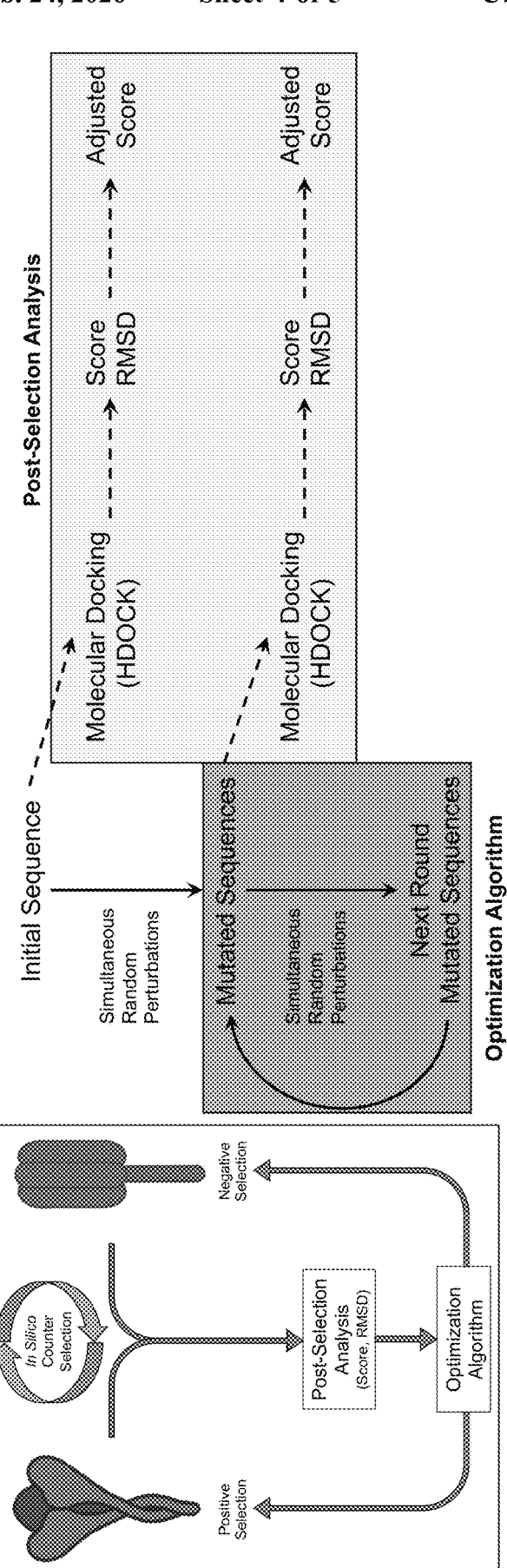
FIG. 4. In Silico Counter-Selection.

Disclosed herein is a method/approach for rapid aptamer selection combining SELEX with recombination and computational methods (referred hereinafter as "recomSELEX"). The recomSELEX method reduces the time required for aptamer identification, is lower in cost, and is capable of exploring oligonucleotide sequences beyond the initial random oligonucleotide library.

The aptamers useful herein have targets that can, in some aspects, include organisms (such as known and emerging pathogens), tumorigenic cells, biomarkers (such as proteins, peptides, nucleotides), as well as drugs, vitamins and other organic and inorganic compounds. Additionally, the evolved aptamers have a wide range of applications that not only includes basic research, but also ensuring food safety and environmental monitoring, important roles as clinical diagnostics (e.g., real-time detection of the pathogen and/or cancer cells), and as therapeutic agents (e.g., bacteria-targeted cytotoxicity and chemotherapy).

In one embodiment, the computational part of the recom-SELEX method consists of a genetic optimization method with novel constraints that is coupled with an oligonucleotide secondary structure predictor for the simultaneous evaluation of the oligonucleotide structure.

The recomSELEX method optimizes the oligonucleotide sequence in a process akin to biological evolution in order to achieve an oligonucleotide sequence that provides the designed structure within the specified constraints. The recomSELEX method also assigns nucleotides to an amino acid sequence based on the probability of intermolecular force interaction. This function enables the user to design aptamers around a specific amino acid/peptide target. The advantage of the recomSELEX method is the rapid evaluation of tens of thousands of oligonucleotide sequences for a specific target in a matter of minutes. In another aspect, this computational method can also be applied to evaluate existing oligonucleotides to generate additional sequences that may have improved specificity and affinity for the target.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a target" or "an aptamer," includes, but is not limited to, mixtures or combinations of two or more such targets or aptamers, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Now having described the aspects of the present disclosure, in general, the following describe some additional aspects of the present disclosure. While aspects of the present disclosure are described in connection with the following and the corresponding text and figures, there is no intent to limit aspects of the present disclosure to this description. On the contrary, the intent is to cover all alternatives, modifications, and equivalents included within the spirit and scope of the present disclosure.

The following descriptions are put forth so as to provide those of ordinary skill in the art with a complete disclosure and description of how the compounds, compositions, articles, devices and/or methods claimed herein are made and evaluated and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The following provides integrating recombinatorial and computational SELEX into recomSELEX. The technical aspects of the two components of the platform: the experimental part (recombinatorial SELEX), the computational part (computational SELEX), and how in their combined form (recomSELEX) they are mutually supportive, are highlighted as follows:

Platform Part 1: Recombinatorial SELEX:

Rationale: recombinatorial SELEX is an aptamer screening approach that exponentially increases the sequence space that is explored by incorporation of a DNA shuffling step that allows recombination between aptamers. Subsequently, recombinatorial SELEX can be employed to develop new and optimize already existing aptamers. Briefly, to rapidly identify aptamers with high specificity and affinity against targets of interest, a DNA shuffling step is added to a counter-, positive-, and counterselection SELEX method, highlighted. Following the second counter-selection, a recombination step is introduced to maintain variation in the selected aptamer population. This recombination step enables the SELEX method to screen an exponentially larger sequence space and thereby many more potential oligonucleotide aptamers then the initial population. As the SELEX rounds progress, the DNA shuffling focuses on a small population of aptamers that were selected based on their affinity for the target.

Recombinatorial SELEX development and aptamer screening. The innovation of recombinatorial SELEX resides in a recombination step between aptamers, allowing the interchange and combination of aptamer sequences with high target affinity. This recombination exponentially increasing the explorable sequence space. Importantly, this approach is used to generate new aptamers, while consistently maintaining the select high affinity population.

Aptamer characteristics: Aptamers against specific targets of interest are screened. New probes will be screened for starting with a ssDNA aptamer library that has a central region of 40 randomized nucleotides, flanked by forward and reverse primer of 19 nucleotides in length which enable PCR-mediated amplification. To improve upon these aptamers, the ssDNA library contains a central region composed of known specific motifs plus a variable length of randomized nucleotides flanking the motifs (the total length of the central region is 40 nucleotides); this central region is flanked by the same forward and reverse 19 nucleotide primers for PCR.

Figure 1:
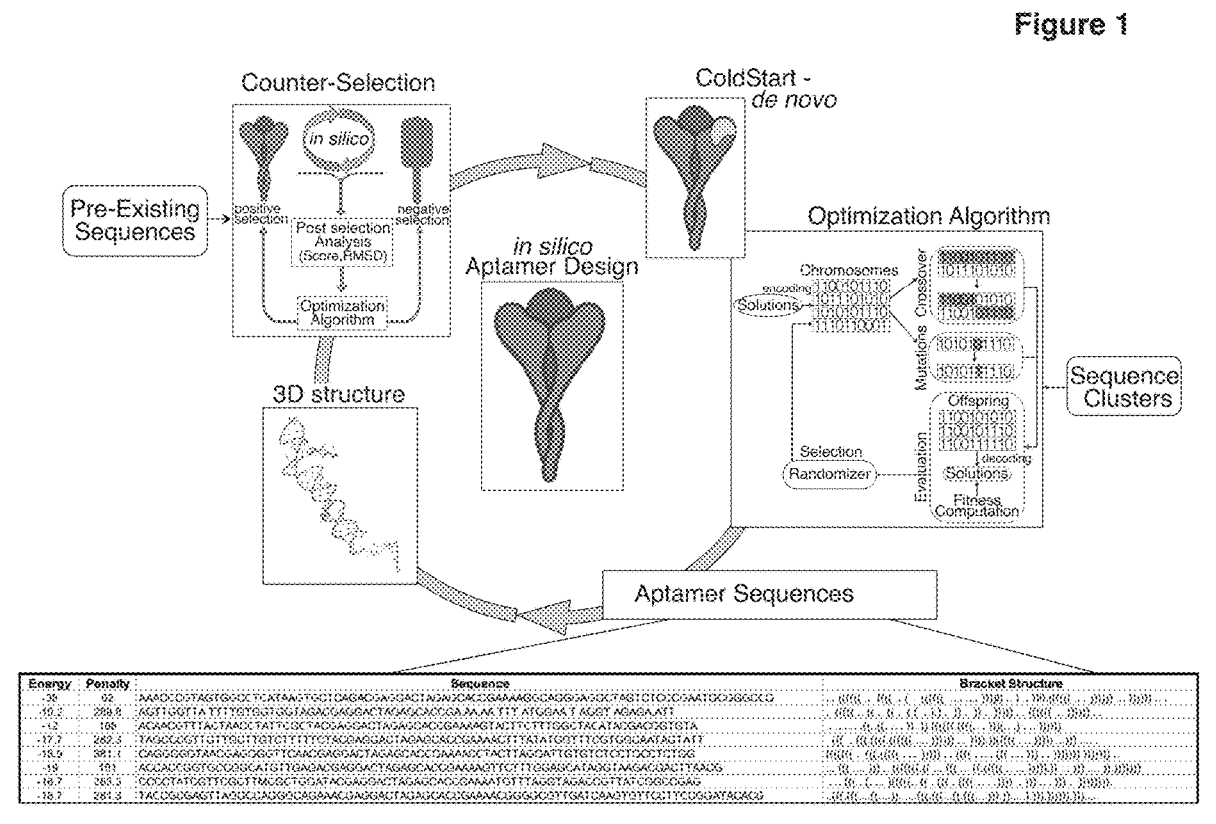

Selection strategy: recombinatorial SELEX consist of 4-steps (FIG. 1): two counter-selection steps, where aptamers with no or low target-specificity are removed from the library; a positive selection step where aptamers with high affinity are selected; and a DNA shuffling step that allows recombination between enriched aptamers. These steps are combined with Illumina sequencing for fast and efficient aptamer identification and bioinformatic analysis for aptamer characterization.

$1^{st}$ counter selection: A starting library of 5 nmol containing ~$10^{15}$ molecules, is counter-selected against biotin-streptavidin-coated magnetic beads in selection buffer (for subsequent protein target selection) or against a bacterial mixture excluding the target-species.

Positive selection: Unbound aptamers are used for positive selection by exposing them to the target. In the case of protein 10 μg of immobilized target is incubated with the library (e.g., proteins are biotinylated and then incubated with streptavidin-coated magnetic beads). In subsequent rounds stringency is increased by reducing incubation time from 1 hr to 20 min and decreasing target concentration. To select for pathogen specific aptamers, the library is incubated with the target bacterium at reducing concentrations in subsequent rounds. To minimize strain specificity an equal ratio of different strains from the same species are used as a positive target. To minimize selection for a specific growth phase, the target mixture contains an equal ratio of early and late exponential phase, and stationary phase cells. Unbound aptamers are washed away at low stringency conditions, DNA-target protein complexes are subsequently eluted from the beads and enriched ssDNA molecules are precipitated and purified. For pathogen targets, the bound ssDNAs are eluted by heating the DNA-pathogen complexes, after centrifugation the supernatant containing the pathogen-bound aptamer fraction is collected, and enriched ssDNA molecules are precipitated and purified.

$2^{nd}$ counter selection: To ensure that aptamers are target-specific, the resulting aptamer library is counter-selected against an unspecific target. This unspecific target is selected based on its high abundance in the natural environment of the specific target. For example, Interleukin 1 alpha (IL-1α) does not show differential expression in blood between different infection etiologies and non-infected patients[4], which makes it an ideal protein for counter selection when targeting biomarker for infectious etiology. For pathogen library is counter-selected following the same conditions as the first counter-selection.

DNA shuffling: A typical SELEX of a $10^{15}$ library needs 12 to 14 selection rounds to sufficiently enrich for a high affinity aptamer. For instance, an aptamer with a dissociation constant ($K_d$) of 1 nM can only be enriched ~100-fold in a single round of selection compared to an aptamer with a $K_d$ of 100 nM.[5] Moreover, increasing selection-rounds introduces undesirable bias including loss of rare sequences[6]. In this experimental part, the maintenance and enrichment of a specific motif in a population is solely dependent on the motif's affinity for the target. Recombinatorial SELEX minimizes the loss of rare sequences with high affinity and allows for exponential enrichment with a few rounds of selection and shuffling.

Recombination between aptamers relies on two essential steps; a random generation of strand breaks in the aptamers obtained following the $2^{nd}$ counter selection, and a ligation step that incorporates different fragments and generates new combinations of aptamers. To avoid DNA degradation, and at most a single nick per molecule, the procedure is performed at suboptimal conditions, while a dephosphorylation step limits ligase activity to newly generated nicks, preventing the generation of large DNA polymers. The resulting library possesses two types of aptamers: 1) due to suboptimal conditions a subset of aptamers will not have recombined; 2) a subset has recombined, generating increased variability in the pool. Within the recombined aptamers, some will have acquired motifs with high specificity and affinity for the target, another set may have lost the screened motifs, while a third set contains new sequences with new desired motifs. This new library is subsequently used in a new round of enrichment.

Recombinatorial SELEX timing and goals: The first round of selection (two counter-selections and a positive selection step), is done in 3 hrs. Subsequent rounds are done in 1.5 hrs. After two completed rounds of selection a recombination step is added, which can be achieved in 3.5 hrs. Initial experiments include 10 rounds of recombinatorial SELEX, with a total of four recombination steps, which can be performed in 2 days. Subsequently, libraries are Illumina sequenced, and analyzed with Aerobio[5], a streaming sequence analysis platform which can automatically group, count and rank similar sequences such as aptamers. It was estimated that four to six rounds of recombinatorial SELEX are enough to enrich for aptamers with high affinity. For proteins targets, it is expected to obtain aptamers with a $K_d$ of several pM, for bacterial specific aptamers, it is expected a $Kd \leq 20$ nM, which are able to detect bacterial cells in the order of $10^2$ to $10^5$ cells/ml[7,8]. After sequence analysis, enriched aptamers are bioinformatically characterized, including structure predictions, stability and free energy calculations, and evolutionary lineage determination using SMART-Aptamer V2.0[9] to identify high-affinity motifs and highly specific aptamers.

Aptamer characterization: 1. Aptamer Specificity: Targets are immobilized on streptavidin-coated magnetic beads and either incubated with a single fluorescence-conjugated enriched candidate aptamer, or the starting aptamer library (negative control). Fluorescence intensity of beads is measured by flow cytometry (FACSVerse, BD). The $K_d$ value of an aptamer is obtained by measuring the fluorescence intensity of a series of different ligand concentrations and analyzed with SigmaPlot software. A similar process is utilized with bacterial targets, replacing the beads for bacterial cells; 2. Aptamer Affinity: To measure competition efficiency, fluorescently labeled aptamers are differentially and simultaneously incubated with a positive and negative target and similarly analyzed with flow cytometry.

Platform Part 2: Computational SELEX:

Rationale: To identify potential single-strand oligonucleotide sequences that are stable and have the desired specificity and affinity, a constrained genetic algorithm (GA) is integrated with the rnafold function using MATLAB. This algorithm recombines oligonucleotide sequences around a target specific core sequence.[10] A genetic algorithm is a stochastic search algorithm based on the mechanism of genetics and natural selection.[11] There are two ways to design the core sequence and the overall process is highlighted in Figure. 1. The first method is to select an accessible amino acid sequence on target protein as visualized using a protein data bank file. This process is conducted in the ColdStart—the de novo Design module. There are several visualization programs available such as pymol, Chimera, and MATLAB. The selection of this amino acid sequence uses a priori knowledge regarding DNA-protein interactions. The second method identifies a conserved core sequence in a series of aptamers (e.g., P12-series) that was previously identified through another SELEX method.[12] Through hundreds to thousands of recombination generations, a list of sequences, structural information, and free energy of folding is generated in a matter of minutes. The sequences are then converted into their two-dimensional and three-dimensional structures. The three-dimensional structures are then imported into an in silico counter-selection module which uses a molecular docking approach. The designed sequence undergoes several rounds of mutations and molecular docking to identify the sequence with the highest affinity for the target and minimized interaction with the non-target protein.

ColdStart—de novo Design The ColdStart—the de novo Design module examines a target protein to identify accessible and biologically relevant atoms and in turn amino acids in the structure. These nucleotides are then aligned to the amino acids (~20) prior to the optimization module which identifies the remaining oligonucleotide sequence. This process is outlined in FIG. 2.

pdb Import: A protein databank (pdb) file is downloaded from, for instance, the Research Collaboratory for Structural Bioinformatics (RCSB)[13] database and uploaded into the ColdStart—de novo design module. High resolution (<5 Angstroms) pdb files should be utilized. These files contain three-dimensional structure information about the protein specifically the coordinates (X, Y, and Z) of the atoms comprising every amino acid visible in the x-ray crystallography structure.

Delaunay Triangulation: The ColdStart module generates a four-column matrix for each atom in the three-dimensional structure using the Delaunay triangulation which maximizes the minimum angle between each atom (point) and adjacent atoms (points). Using the 3D option in MATLAB, does not have any points on the interior of the circumsphere associated with each tetrahedron. Using the Delaunay triangulation avoids sliver triangles.

Alpha Shape: The all-atom, four-column matrix is subjected to an alpha shape algorithm, which generates a bounding volume of the outer surface that envelopes the proteins three-dimensional points. The volume of the alpha shape can be manipulated by increasing or decreasing the alpha term which will include more or less points depending on the manipulation. The product of this step includes all atoms on the periphery of the protein.

Filter. A filter is incorporated to retain all biologically relevant atoms. Biologically relevant atoms are oxygen and nitrogen on hydrophilic amino acids. These specific amino acids are selected due to their propensity to form hydrogen bonds and be on the external surfaces of the protein.

Solid Angle Calculation: The solid angle is calculated for all biologically relevant atoms using the Delaunay triangulation data. For a given atom, the angle of all surrounding atoms is determined. A completely surrounded, or internal, atom would have a sphere of other atoms around it with a calculated solid angle of 4pi. The biologically relevant atoms are then filtered for their accessibility. With a surrounded atom having a solid angle of 4pi, an accessible atom is determined to be an atom with a solid angle less than 2pi.

Clustering: Atoms with high solid angles are clustered to identify atoms in adjacent amino acids that can bind/interact with an aptamer. The clustering algorithm finds groups of amino acids that are in close proximity and whose sum of total solid angles is high. An extra constraint is imposed that each cluster must have a minimum number of amino acids and that these amino acids must have a total solid angle greater than a certain threshold. The clustering algorithm identified multiple clusters which are then passed to the amino acid sequence extraction module.

Amino Acid Sequence Extraction: While the clustering module identifies amino acids based on the proximity and accessibility of the biologically relevant atoms, the specific amino acids and their order based on three-dimensional space needs to be determined. A primary amino acid sequence provides no insight into the three-dimensional orientation of the amino acids, consequently the amino acid extraction module establishes an order of amino acids based on the proximity to each other and not their primary sequence order. The goal of this module is to establish a spatial relationship of the amino acids such that the assignment of nucleotides possesses a spatial relationship and is not linear.

Assign Nucleotides: The identified clustered amino acids are paired with an oligonucleotide based on the historic nucleotide/amino acid interaction.[14,15,16] These assigned oligonucleotides then become the core sequence for optimization of the remaining sequence.

Optimization: The optimization module applies a genetic algorithm and constraints to the sequence to ensure the structure of the sequence aligns with the desired application. The process moves through sequential generations identifying elite sequences, inducing mutations, and cross-over to identify the best sequence.

The optimization uses the Genetic Algorithm (GA; MATLAB 2021a) to generate an initial population around the core sequence. The length of the aptamer is input by the user as a prefix sequence (e.g., sequence before the core sequence) and the suffix sequence (e.g., sequence following the core). This option allows the user to relatively direct the position of the core sequence which is designated to interact with the target protein. The nucleotide letters are then converted to numeric digits (1-4) and imported into the GA.

After each generation, the secondary structure is determined using rnafold. The structure is denoted in the dot-bracket format (e.g., . . . ((( . . . ))) . . . ), where unpaired nucleotides are designated by dots and paired nucleotides by brackets. The folding algorithm also provides the free energy of folding for the designated aptamer sequence as an indicator of stability. The secondary structure determination in the optimization step is critical for determining the unpaired oligonucleotides in the potential aptamer sequence.

The sequence and secondary structure are then used to calculate the penalties for violating user defined constraints. The current constraints are preventing quad nucleotides (e.g., the same nucleotide four times in a row), an unpaired tail on the 5'-end of the oligonucleotide sequence, percent of cytosine-guanine, unpaired percent of the core sequence. The user has the capability of turning the constraints on and off as well as altering constraints such as CG content and unpaired core. Each violation induces a 100 kcal/mol energy penalty that is summed and then added to the stability energy score.

The score is determined for each sequence in each generation. For each generation, the GA optimization identifies the elite sequences (5%), induces mutations in 15% of the sequences, and allows cross-over in the remaining 80% of the sequences. The elites are the sequences with the best scores and the sequences are carried to the next generation unchanged. The goal of the optimization is to achieve the best score which is the most stable sequence with the minimum penalties.

The optimization occurs until one of three conditions is met. The first condition is the optimization score goal is achieved. However, this can also be set to infinity. The second condition is that the number of stall generations has been reached which occurs when the score fails to improve through the designation number of generations. The third and final condition is when the number of generations has been reached.

An additional option of the optimization algorithm enables the user to input sequences and use the constraints to modify as necessary. For example, the use of an aptamer on a graphene biosensor required the 5'-end of the oligonucleotide be unpaired for the attachment of an amine group to covalently bind the molecule to a pyrene linker molecule. The aptamers 1C and 4C were selected as a proposed therapeutic and have high affinity for the Spike protein. These aptamers, however, do not have an unpaired 5'-end. Subsequently, the genetic algorithm was used to add a 5 and 7 nucleotide sequence to the 5'-end of the 1C and 4C oligonucleotides respectively without altering the remaining structure. Flow cytometry as used to confirm affinity for the Spike protein remained high, FIG. 3, as well as constructed "anti-sense" sequences to show the algorithm did better maintain the high affinity than random sequences.

Two Dimensional Structures: Upon completion of the optimization algorithm, the optimized nucleotide sequence is then once again converted to the secondary structure in dot-bracket structure. The secondary structure is determined using rnafold (MATLAB 2021a)

Three Dimensional Structures: While the secondary structure provides the interaction between nucleotides, the tertiary structure provides the relative positioning of each atom composing the oligonucleotide in a pdb file format. The tertiary structure is generated using RNAComposer.[17-18] This program applies the machine translation principle to relate RNA secondary structure and tertiary structure elements from the RNA FRABASE database. These structures can be generated either iteratively (one at a time) or in batches.

Counter-Selection: The counter-selection module accepts the previously generated three-dimensional structure and runs through a series of molecular docking and simultaneous perturbation steps. The original structure is the baseline, and the subsequent mutated sequences are compared to the original or best docking score. The algorithm introduces mutations over multiple iterations to find the best interaction between the sequence and target while reducing the interaction with non-target proteins. This module is highlighted in FIG. 4.

Initial Sequence: The counter-selection module can accept sequences from either the previous optimization following ColdStart or a user defined sequence. The user input sequence is an option to use the process to improve an existing aptamer and determine its potential binding against a non-target protein to improve specificity. The user in this step has the ability to subject the sequence to multiple non-target proteins.

Figure 5:
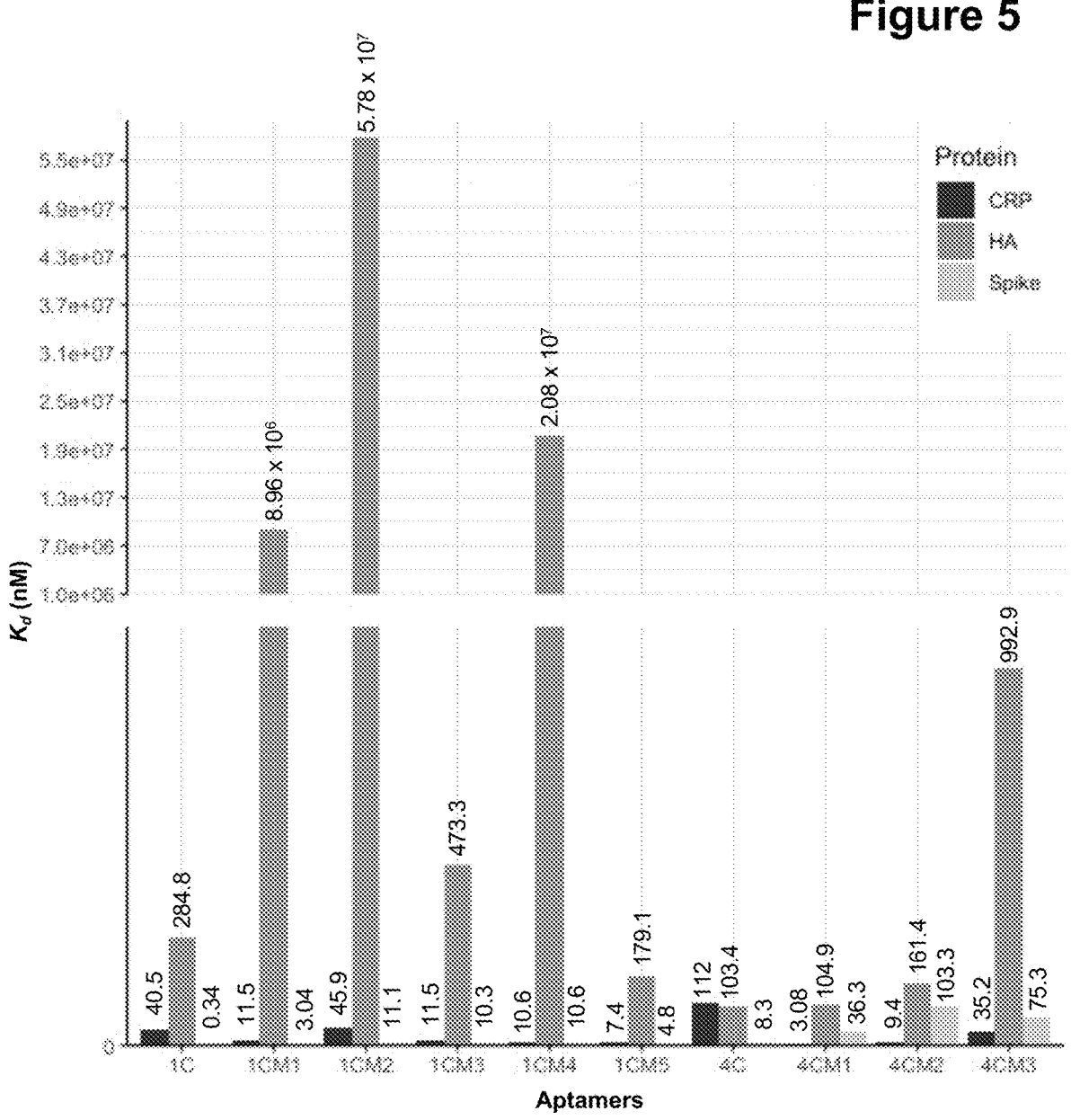
FIG. 5. Experimental dissociation constants (Kd) values for 10 ssDNA oligonucleotides binding either Spike, HA, or CRP. The values were used to calculate rank correlation with the molecular docking software.

The sequence and corresponding pdb file are then directed into a molecular docker, HDOCK. Using a parallel loop, the molecular docking runs the positive and negative selection docking simultaneously. The user can identify the positive and negative target proteins and their corresponding pdb file from the Protein Databank. Upon completion of the simulations, the energy interaction score (kcal/mol) and the root mean square distance (RMSD) of the docking are extracted from the generated pdb files. The final scores can be calculated by weighting the energy and RMSD values such that they are not equal. To validate the counter-selection process, we generated 10 different aptamers and conducted molecular docking against Spike protein, Hemagglutinin, and C-Reactive Protein. The Kd values were also determined using flow cytometry (FIG. 5). Using both Spearman and Kendall rank correlation the docking score and Kd values were rank-ordered. The correlation enables weighting both the energy interaction score and RMSD to generate an adjusted score. Rank ordering demonstrates a change in docking corresponds to a change in Kd value even though the magnitude of the change in the dissociation constant is not determined.

Simultaneous Perturbations: Once the initial sequence has completed the positive and negative counter-selection molecular docking, perturbations or mutations are introduced into the sequence. The user can define the number of mutations which can be in the core or non-core part of the oligonucleotide. The user also defines the number of sequences to be generated. Since molecular docking can be computationally expensive (e.g., time) it is necessary to select a manageable number of sequences based on the user's computational capacity.

The secondary structure for each sequence is then generated using rnafold. The sequence and structure are then converted to a three-dimensional pdb file via RNAComposer. The sequence and structures are exported to RNA-Composer and downloaded from the server using a python script. Each sequence is docked using HDOCK against both the positive and negative protein target. The energy score and RMSD is extracted from each docking simulation. The docking is done in parallel to reduce the run time.

Optimization: Upon completion of the simultaneous perturbation molecular docking step, the sequences and their corresponding scores are analyzed. The analysis/optimization attributes the corresponding scores for a given sequence to the mutations in the sequence from the original. The optimization then selects the mutations that induced the greatest improvements in the scores. A new sequence with these mutations is then generated as well as the corresponding secondary structure. The corresponding three-dimensional structure is generated using RNAComposer and downloaded as a pdb file. The generated sequence then undergoes the positive and negative selection molecular docking and scores are extracted. If the scores are better than the original, then the optimized sequence then replaces the original for the next round of perturbations. The user designates the number of rounds of perturbations and optimizations.

Aptamer characterization: Oligonucleotide affinity and specificity for the design targets is determined using a flow cytometry (FACSVerse, BD) binding assay. The $K_d$ values for the aptamer against the target and non-target protein are determined by measuring the fluorescence intensity with a series of different ligand concentrations.

REFERENCES

1. Ellington, A D and Szostak, J W (1990). In vitro selection of RNA molecules that bind specific ligands. Nature 346: 818-822.
2. Tuerk, C and Gold, L (1990). Systematic evolution of ligands by exponential enrichment: RNA ligands to bacteriophage T4 DNA polymerase. Science 249: 505-510.
3. Cho, E. J., Lee, J.-W. & Ellington, A. D. Applications of aptamers as sensors. Annu. Rev. Anal. Chem. 2, 241-264 (2009).
4. Slaats, Jeroen, et al. "IL-1β/IL-6/CRP and IL-18/ferritin: distinct inflammatory programs in infections." PLoS pathogens 12.12 (2016).
5. Irvine, D., Tuerk, C., & Gold, L., 1991. Selexion: Systematic evolution of ligands by exponential enrichment with integrated optimization by non-linear analysis. Journal of molecular biology, 222(3), 739-761.

6. Wang, J., Gong, Q., Maheshwari, N., Eisenstein, M., Arcila, M. L., Kosik, K. S., & Soh, H. T., 2014. Particle Display: A Quantitative Screening Method for Generating High-Affinity Aptamers. Angewandte Chemie International Edition, 53(19), 4796-4801.
7. Liu, D., Hu, B., Peng, D., Lu, S., Gao, S., Li, Z., . . . & Jiao, B., 2020. Isolation ssDNA aptamers specific for both live and viable but nonculturable state Vibrio vulnificus using whole bacteria-SEILEX technology. RSC Advances, 10(27), 15997-16008.
8. Mirzakhani, K., Gargari, S. L. M., Rasooli, I., & Rasoulinejad, S., 2018. Development of a DNA aptamer for screening Neisseria meningitidis Serogroup B by cell SELEX. Iranian biomedical journal, 22(3), 193.
9. Song, Y., Song, J., Wei, X., Huang, M., Sun, M., Zhu, L., . . . & Yang, C., 2020. Discovery of Aptamers Targeting Receptor-Binding Domain of the SARS-CoV-2 Spike Glycoprotein.
10. Ellington, A D and Szostak, J W (1990). In vitro selection of RNA molecules that bind specific ligands. Nature 346: 818-822.
11. Tuerk, C and Gold, L (1990). Systematic evolution of ligands by exponential enrichment: RNA ligands to bacteriophage T4 DNA polymerase. Science 249: 505-510.
12. Cho, E. J., Lee, J.-W. & Ellington, A. D. Applications of aptamers as sensors. Annu. Rev. Anal. Chem. 2, 241-264 (2009).
13. H. M. Berman, J. Westbrook, Z. Feng, G. Gilliland, T. N. Bhat, H. Weissig, I. N. Shindyalov, P. E. Bourne (2000) The Protein Data Bank Nucleic Acids Research, 28: 235-242.
14. Luscombe N M, Laskowski R A, Thornton J M. Amino acid-base interactions: a three-dimensional analysis of protein-DNA interactions at an atomic level. Nucleic Acids Res. 2001; 29(13):2860-2874. doi:10.1093/nar/29.13.2860.
15. Hoffman M M, Khrapov M A, Cox J C, Yao J, Tong L, Ellington A D. AANT: the Amino Acid-Nucleotide Interaction Database. Nucleic Acids Res. 2004; 32 (Database issue): D174-D181. doi:10.1093/nar/gkh128.
16. Park, B., Kim, H. & Han, K. DBBP: database of binding pairs in protein-nucleic acid interactions. BMC Bioinformatics 15, S5 (2014).
17. Antczak, M., Popenda, M., Zok, T., Sarzynska, J., Ratajczak, T., Tomczyk, K., Adamiak, R. W., Szachniuk, M. New functionality of RNAComposer: an application to shape the axis of miR160 precursor structure, Acta Biochimica Polonica, 2016, 63(4):737-744 (doi: 10.18388/abp.2016_1329).
18. Popenda, M., Szachniuk, M., Antczak, M., Purzycka, K. J., Lukasiak, P., Bartol, N., Blazewicz, J., Adamiak, R. W. Automated 3D structure composition for large RNAs, Nucleic Acids Research, 2012, 40(14):e112 (doi:10.1093/nar/gks339).

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for selecting and identifying aptamers with high specificity and affinity against a target of interest, said method comprising:

a) Performing recombinatorial SELEX (Systematic Evolution of Ligands by EXponential enrichment) for screening, selecting, identifying, and characterizing aptamers against the target of interest, and b) Integrating Computational SELEX with a constrained genetic algorithm (GA) to further identify and characterize the aptamers that are stable and have the desired specificity and affinity against the target of interest, wherein the constrained genetic algorithm (GA) recombines oligonucleotide sequences around a target specific core sequence, and wherein the core sequence is designed and conducted in a de novo design module ("ColdStart") that selects an accessible amino acid sequence on target protein as visualized using a protein data bank file.

2. The method of claim 1, wherein recombinatorial SELEX comprises two-counter-selection steps, a positive selection step, and a DNA shuffling step.

3. The method of claim 2, wherein aptamers with no or low target-specificity are removed in the two-counter selection steps.

4. The method of claim 2, wherein aptamers with high affinity are selected in the positive selection step.

5. The method of claim 2, wherein the DNA shuffling step is added to a counter-, positive-, and counterselection steps that allows recombination between aptamers.

6. The method of claim 5, wherein the recombination between aptamers exponentially increases explorable sequence spaces.

7. The method of claim 2, wherein the counter-selection steps, the positive selection steps and the DNA shuffling step are combined with sequencing for fast and efficient aptamer identification and bioinformatic analysis for aptamer specificity and affinity.

8. The method of claim 1, wherein recombinatorial SELEX is performed for 1-10 rounds.

9. The method of claim 1, wherein the constrained genetic algorithm (GA) is integrated with rnafold function.

10. The method of claim 1, wherein the core sequence is designed with a method that identifies a conserved core sequence in a series of aptamers previously identified through another SELEX method.

11. The method of claim 1, wherein a list of sequences, structural information and free energy of folding is generated through recombination generations.

12. The method of claim 11, wherein the sequences are converted into their two- and three-dimensional structures, which then imported into an in silico counter-selection module.

13. The method of claim 12, wherein the in silico counter-selection module uses a molecular docking approach.

14. The method of claim 13, wherein designed sequence undergoes several rounds of mutations and molecular docking to identify the sequence with a highest affinity for the target and minimize interaction with a non-target.

15. The method of claim 14, further comprises an optimization module that applies a genetic algorithm and constraints to the sequence to ensure the structure of the sequence aligns with a desired application.

16. The method of claim 15, wherein the optimization process moves through sequential generations identifying elite sequences and cross-over to identify a best sequence.

17. The method of claim 1, wherein the target of interest is selected from the group consisting of ions, small molecules, membrane receptors, peptides, proteins, microorganisms, pathogens, cells, oligonucleotides, drugs, and environmental contaminants.

18. The method of claim 17, wherein the microorganism comprises bacteria or viruses.

\* \* \* \* \*